United States Patent [19]

Heyman

[11] 4,113,952
[45] Sep. 12, 1978

[54] PROCESS FOR PREPARING 2-BENZIMIDAZOLONES

[75] Inventor: Duane A. Heyman, Waterville, Ohio

[73] Assignee: The Sherwin-Williams Company, Cleveland, Ohio

[21] Appl. No.: 818,172

[22] Filed: Jul. 22, 1977

[51] Int. Cl.² .................................. C07D 235/26
[52] U.S. Cl. .................................................. 548/305
[58] Field of Search ...................................... 548/305

[56] References Cited

FOREIGN PATENT DOCUMENTS 811,692  4/1959  United Kingdom .................. 548/305

OTHER PUBLICATIONS

Wallis et al. In: Adams et al. Organic Reactions vol. III, pp. 267–279 N.Y., Wiley, 1946.
Wright Chem. Rev. 1951, vol. 48, pp. 456–458.

Primary Examiner—Natalie Trousof
Attorney, Agent, or Firm—James V. Tura; Neil A. DuChez

[57] ABSTRACT

This invention is directed to a process for preparing 2-benzimidazolone which comprises reacting 2'-carbamoylphthalanilic acid in an alkaline medium with a metal hypohalite.

19 Claims, No Drawings

PROCESS FOR PREPARING 2-BENZIMIDAZOLONES

This invention relates to a process for preparing 2-benzimidazolone by reacting 2'-carbamoylphthalanilic acid in an alkaline medium in the presence of a Hofmann reagent.

The present procedures for the synthesis of 2-benzimidazolone comprise reacting 1,2-diaminobenzene with a carbonyl source such as urea, phosgene, carbon dioxide, etc., see Beilsteins Handbook of Organic Chemistry, Vol. 24, page 116, (1936); Junker et al., German Offen. No. 2,052,026 (1972); German Pat. No. 1,058,510 and French Pat. No. 1,470,892. A major commercial disadvantage of using 1,2-diaminobenzene as a chemical intermediate is that it is prepared from a chemical by-product, i.e. 2-nitroaniline, with an uncertain future. Moreover, at this time, the toxicity and future availability are in question. An alternative method for preparing 2-benzimidazolone, which is not very appealing from a commercial standpoint, involves heating an azide with phthalic anhydride in an appropriate solvent to obtain yields ranging up to 80%. The use of azides, however, are dangerous particularly when working with the compounds on a commercial scale; see Maffei et al, Ann. Chim., 49, 1809–1814 (1959).

The search for a commercially useful 2-benzimidazolone precursor that was not based on a chemical by-product eventually led to 2-aminobenzamide. This benzamide can be visualized as a simple precursor to benzimidazolone by carrying out a Hofmann rearrangement on the amide group. Availability would not be a problem with 2-aminobenzamide as it is readily prepared from isatoic anhydride, a commercial chemical in good supply.

Attempts to react 2-aminobenzamide under Hofmann amide rearrangement conditions with sodium hypochlorite, sodium hypobromite or methyl hypobromite produced very small yields of benzimidazolone. The predominant reaction appeared to be a reaction of the hypohalite with the amino group rather than with the amido group. In an attempt to avoid the amino group hypohalite reaction some amino protecting groups were used. The most common protecting group is the acyl substituent. The N-acetyl derivative was readily prepared from aminobenzamide and acetic anhydride. Another type of protected amino group is a Schiff's base. The Schiff's base was readily prepared in good yield from 2-aminobenzamide and benzaldehyde. Both of these amino protected compounds, when reacted under Hofmann rearrangement conditions with a hypohalite resulted not in the desired N-substituted benzimidazolones but in modest yields of 2-substituted-4-quinazolinones.

Thus, contrary to the previously described N-acyl benzamide, 2'-carbamoylphthalanilic was found to react with the hypohalites to give 2-benzimidazolone. Accordingly, it is an object of this invention to provide a process for preparing 2-benzimidazolone from 2'-carbamoylphthalanilic acid.

More specifically, the invention relates to a process for preparing 2-benzimidazolone which comprises reacting 2'-carbamoylphthalanilic acid in a liquid alkaline medium with about a chemical equivalent of Hofmann reagent, i.e. an alkali or alkaline earth metal hypohalite such as sodium or calcium hypochlorite over a wide range of temperatures. The reaction is substantially adiabatic and can proceed to completion without the addition of heat. However, the alkaline mixture may be heated to temperatures ranging up to the reflux temperatures, e.g. where the liquid medium is water the temperature may range up to 100° C. and subsequently cooled. The cooled alkaline reaction mixture is acidified by the addition of an acidic material, e.g. an acid, to lower the pH and precipitate the 2-benzimidazolone.

The initial step in the overall reaction scheme involves the preparation of 2-aminobenzamide which is obtained in yields ranging from 90 to 95% by reacting isatoic anhydride with ammonia at moderate temperatures. This reaction is illustrated by the following equation; see Staiger et al., Journal Organic Chemistry, 13, 347 (1948).

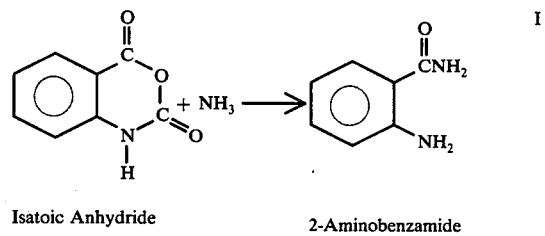

Isatoic Anhydride      2-Aminobenzamide

The 2-aminobenzamide is then converted to an amino protected benzamide, i.e. 2'-carbamoylphthalanilic acid by reacting the aminobenzamide with phthalic anhydride in a solvent, e.g. various aromatic hydrocarbons, halogenated hydrocarbons, alcohols, etc. The 2'-carbamoylphthalanilic acid is obtained from this reaction in yields of 90% or better at temperatures ranging from ambient, e.g. 25° C., up to 80° C. and at ratios of phthalic anhydride to 2-aminobenzamide of 1.0 to 3.0; see Kurihara, Journal of Organic Chemistry, 34, 2123, (1969). The reaction can be illustrated as follows:

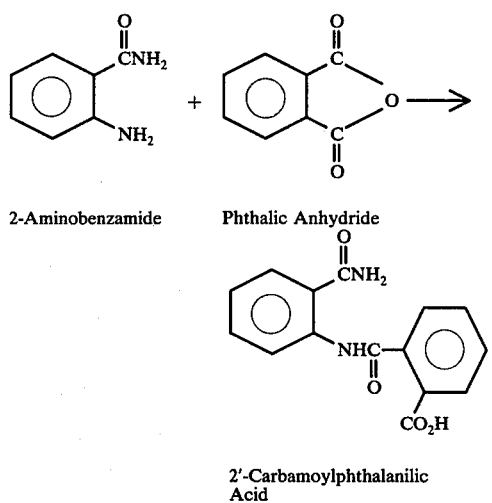

2-Aminobenzamide     Phthalic Anhydride

2'-Carbamoylphthalanilic Acid

An essential part of the overall reaction, in accordance with this invention, consists of the following. The 2-carbamoylphthalanilic acid is mixed with an aqueous or an aqueous-alcoholic solution of 1 to 4 chemical equivalents of an alkaline material. The alcohol may be an aliphatic alcohol having 1 to 3 carbon atoms per molecule. The alkaline material consists of various basic compounds such as the alkali metal hydroxides, the carbonate and the organic alkaline materials such as the tertiary aliphatic amine, e.g. trimethyl or triethyl amine, etc. This mixture forms either a slurry or a clear solution depending on the amount of solvent used. The reaction can be run through to completion at temperatures ranging from as low as the freezing point, depending on the composition of the liquid medium, to as high as the boiling or reflux temperatures of the reaction mixture. Preferably, the reaction is carried out at about room temperature or below, e.g. 0°-25° C. to minimize any base catalyzed hydrolysis of the phthalanilic acid or any base catalyzed ring closure to the 2-substituted-4-quinazolone. Subsequently, about one chemical equivalent of a metallic hypohalite solution, e.g. sodium hypochlorite solution, having a normality ranging from about 0.5 to 2.0 N is added the mixture of the carbamoylphthalanilic acid.

In addition, the hypohalite reactant also can be prepared in situ, for example, by reacting chlorine gas with the alkaline mixture which comprises at least two chemical equivalents of the alkali metal compound e.g. sodium hydroxide and the 2'-carbamoylphthalanilic acid. As the exotherm caused by adding the hypohalite to the alkaline carbamoylphthalanilic acid mixture peaks out, an additional quantity of up to two chemical equivalents of the alkali metal compound is added to the reaction mixture. The stoichiometry of this amide-hypohalite reaction requires about three equivalents of the alkaline or basic compound. At least one equivalent of the alkaline compound is added during the preparation of the carbamoylphthalic acid solution. The second equivalent of the base is formed during the hypohalite chlorination of the amide group. The third equivalent and any excess of the basic compound can be added either prior to the bleaching or after bleaching. The preferred method, however, is to add the basic compound before and after the addition of the hypohalite to minimize the possible hydrolysis of 2'-carbamoylphthalanilic acid and to minimize any alkaline retardation of the hypohalite chlorination reaction.

After all the reactants have been added to the reaction mixture, the reaction is allowed to proceed either adiabatically or it can be accelerated by the addition of heat. Additional heating to temperatures ranging up to reflux (usually 50°-70° C.) is applied for a short period, e.g. up to thirty minutes after the reaction exotherm subsides to assure completion of the rearrangement reaction.

The reaction mixture is then cooled to about room temperature and acidified, e.g. by the addition of an acid to a lower pH ranging down to a pH of 9 and as low as 6. The acidification or the addition of the acid to the reaction mixture to lower the pH precipitates the 2-benzimidazolone in yields ranging up to 98%. The phthalic acid can be recovered by lowering the pH of the mother liquor to below pH 3. The reaction can be illustrated by the following equation.

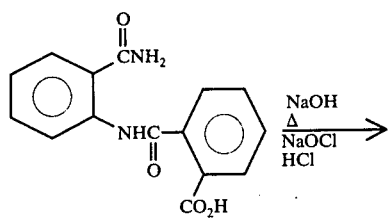

2-Carbamoylphthalanilic Acid

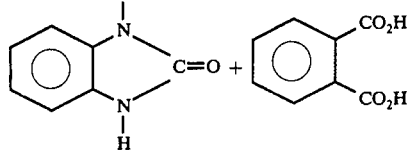

2-Benzimidazolone       Phthalic Acid

The 2-benzimidazolone prepared in accordance with this invention is potentially useful as a chemical intermediate and particularly as an intermediate in preparing ortho-phenylenediamine (1,2-diaminobenzene). In addition, the 2-benzimidazolone is known to be useful as a growth promoter, as a stabilizer for polyamides, as a nucleating agent for crystalline polymers, etc. Other potential uses of the compound include its use as an intermediate for the preparation of various drugs, azo dyes, high temperature polyesters and as bleach activators; see U.S. Pat. Nos. 3,886,131; 3,819,595; 3,860,564 and 3,775,333.

Of these various uses, a particular important use is the conversion of the 2-benzimidazolone to ortho-phenylenediamine by acid hydrolysis as disclosed in copending application by Lubomir Vacek, Ser. No. 818,173, filed July 22, 1977.

The following examples illustrate the process for preparing 2-benzimidazolone in accordance with this invention.

EXAMPLE I

Preparation of 2'-Carbamoylphthalanilic Acid

Phthalic anhydride, 15.5 g (0.10 mole) was dissolved in 80 ml of warm 1,1,2-trichloroethane (45° C.), filtered to remove a small amount of insoluble material (phthalic acid) and the filtrate mixed with an additional 70 ml of solvent. To the room temperature phthalic anhydride solution was added with mechanical stirring a warm (60° C.) solution of 13.6 g (0.10 mole) of 2-aminobenzamide in 150 ml of 1,1,2-trichloroethane. Within minutes of benzamide addition a solid precipitated. The white suspension was stirred at 60° to 70° C. for 30 minutes and then let cool to room temperature with stirring. The white reaction mixture was filtered, washed with solvent, air dried and dried 16 hours at 50° C. There was collected 25.9 g (91%) of white solid product which was shown to be the desired product by infrared spectroscopy (mp 184.0°-185.0° C.). An additional 2.1 g (7%) of product precipitated from the above filtrate.

The same general procedure was used when using toluene, chloroform, tetrahydrofuran, methylene chloride, acetone, methanol, acetonitrile or dimethylsulfoxide as the reaction solvent.

EXAMPLE II

Preparation of 2-Benzimidazolone

To 125 ml of distilled water at room temperature was added 7.2 ml of 50% aqueous sodium hydroxide and 25.2 g (0.09 mole) of 2'-carbamoylphthalanilic acid. The reaction mixture was stirred 2 to 5 minutes and then was added 60 ml of cool 1.48 N sodium hypochlorite solution immediately turning the reaction mixture brown and exhibiting a 7° exotherm. Within 1 minute of bleach addition, 7.4 ml of additional 50% sodium hydroxide solution was added causing a 15° exotherm. The reaction mixture was stirred for 30 minutes at 70° C., cooled at room temperature and acidified to pH 8.5 precipitating a solid. The solid was recovered by filtration, washed with water, air dried and oven dried 16 hours at 50° C. There was collected 11.6 g (98%) of tan solid shown by an infrared spectrum to be 2-benzimidazolone.

Preparation of Sodium Hypochlorite Solution

To a 300 ml resin kettle fitted with true-borer stirrer, thermometer, gas dispersion tube and exit tube connected to a water bubbler was added 1400 ml of distilled water and 400 g of 50% aqueous sodium hydroxide. After cooling to 5° C. with a dry ice-acetone bath, chlorine was bubbled through the cooled, stirring reaction mixture for 32 to 33 minutes at the rate of 2.05 g/minute (flow meter). The reaction mixture was kept at -30° to 2° C. during chlorine addition by manipulation of the cooling bath. About 10 minutes after chlorine addition was complete a sample of the yellow reaction mixture was taken for analysis. Found 1.79 g/l of free NaOH and 110.36 g/l of NaOCl (1.483 N).

EXAMPLE III

Preparation of 2-Benzimidazolone

To a solution of 1.3 g (0.03 moles) of sodium hydroxide in 50 ml of water at 5° C. was added 8.5 g (0.03 moles) of 2'-carbamoylphthalanilic acid. Calcium hypochlorite, 4 g (Olin "HTH", 54% active chlorine) was added to the cold solution forming a suspension. About 2 minutes after hypochlorite addition 2 g (0.05 moles) of sodium hydroxide was added to the 14° C. tan suspension. After base addition the temperature of the reaction mixture increased to 42° C. over a 10 minute period. The reaction mixture was stirred without heating an additional 50 minutes while the temperature dropped from 42° to 29° C. The suspension was filtered off, washed with water and air dried. The 6.2 g of residue was stirred with about 5 g of sodium hydroxide in 150 ml of water. The suspension was filtered, the calcium residue discarded and the brown filtrate acidified to about pH 5 and filtered. After drying there was collected 1.7 g of tan solid identified as crude 2-benzimidazolone by infrared spectroscopy.

While this invention has been described by a number of specific embodiments, it is obvious that there are other variations and modifications which can be made without departing from the spirit and scope of the invention as set forth in the appended claims.

What is claimed is:

1. A process for preparing 2-benzimidazolone which comprises reacting 2'-carbamoylphthalanilic acid in a liquid alkaline medium with a metal hypohalite selected from the class consisting of alkali metal and alkaline earth metal hypohalites at temperatures ranging up to the reflux temperature of the medium and subsequently cooling and acidifying the medium to precipitate 2-benzmimidazolone.

2. The process of claim 1 further characterized in that the alkaline medium comprises water.

3. The process of claim 1 further characterized in that the alkaline medium comprises an alcohol.

4. The process of claim 1 further characterized in that the alkaline medium comprises water and alcohol.

5. The process of claim 4 further characterized in that the alcohol is an aliphatic alcohol having 1 to 3 carbon atoms per molecule.

6. The process of claim 1 further characterized in that the reaction is substantially adiabatic and is completed without the addition of heat.

7. The process of claim 1 further characterized in that the temperature of the alkaline medium ranges from above the freezing to the reflux temperature.

8. The process of claim 2 further characterized in that the temperature of the alkaline medium ranges up to 100° C.

9. The process of claim 1 further characterized in that the liquid alkaline medium is heated and subsequently cooled and acidified to precipitate the benzimidazolone.

10. The process of claim 1 further characterized in that the metal hypohalite is an alkali metal hypohalite and the alkaline medium comprises an alkali metal hydroxide.

11. The process of claim 1 further characterized in that the metal hypohalite is an alkaline earth metal hypohalite and the alkaline medium comprises an alkali metal hydroxide.

12. The process of claim 11 further characterized in that the alkaline earth metal hypohalite is calcium hypohalite.

13. The process of claim 2 further characterized in that the alkaline medium comprises a tertiary aliphatic amine.

14. The process of claim 1 further characterized in that the metal hypohalite is an alkaline earth metal hypochlorite.

15. The process of claim 2 further characterized in that the alkaline medium comprises an alkali metal carbonate.

16. The process of claim 13 further characterized in that the tertiary aliphatic amine is triethyl amine.

17. The process of claim 1 further characterized in that the metal hypohalite is a metal hypochlorite prepared in situ by adding chlorine to the liquid alkaline medium comprising an alkali metal compound.

18. The process of claim 17 further characterized in that the alkali metal compound is sodium hydroxide.

19. The process of claim 2 further characterized in that the alkaline medium comprises an alkali metal hydroxide.

* * * * *